US006223084B1

(12) United States Patent
Lepore et al.

(10) Patent No.: US 6,223,084 B1
(45) Date of Patent: Apr. 24, 2001

(54) APPARATUS FOR THE BLOODLESS, NON-INVASIVE CORRECTION OF ALTERATIONS OF THE ARCH OF THE FOOT

(75) Inventors: Antonio Lepore, Santa Maria Capua Vetere; Francesco Pettrone, Pignataro Maggiore; Ivo Rendina, Naples; Antonio Vozza, Casagiove, all of (IT)

(73) Assignee: Correctionpes S.R.L., Caserta (IT)

( * ) Notice: Subject to any disclaimer, the term of this patent is extended or adjusted under 35 U.S.C. 154(b) by 0 days.

(21) Appl. No.: 09/314,477

(22) Filed: May 18, 1999

(30) Foreign Application Priority Data

Jun. 17, 1998 (EP) .................................................. 98111096

(51) Int. Cl.$^7$ ....................................................... A61N 1/36
(52) U.S. Cl. ............................................... 607/62; 607/70
(58) Field of Search .................................. 607/43, 49, 51, 607/52, 62, 68, 70

(56) References Cited

U.S. PATENT DOCUMENTS

| 4,153,060 | * | 5/1979 | Korostoff et al. | 607/51 |
| 4,167,189 | * | 9/1979 | Tachi et al. | 607/62 |
| 4,919,139 | * | 4/1990 | Brodard | 607/70 |

* cited by examiner

Primary Examiner—William E. Kamm
(74) Attorney, Agent, or Firm—Arthur S. Cookfair

(57) ABSTRACT

An apparatus for the correction of alterations of the arch of the foot comprises a source of electric current with multiple step waveforms of variable duration and amplitude pulses, said source is connected to electrodes to be placed on the body of the patient to be treated, Detectors of the resistance existing at the ends of said electrodes during the use of the apparatus measuring means and transducers of the data supplied by the detectors and means for processing the resistance parameters obtained produce self-regulation of the generated waveforms. The electrodes are placed on different points of the patient's leg and foot according to the existing alteration. The apparatus allows a method based on electrostimulations with stepped pulse wave forms for treating and healing non-malforming alterations of the foot. The therapeutic action of the apparatus is based on the stimulation caused by the electric pulses properly applied and self-regulated by microcircuits operating feedback processes, through inputs of detecting sensors, measuring devices and transducers of the resistance existing at the electrodes. The stimulation evokes the myotatic reflex through rapid and time-limited stretching of the musculo-tendinous tracts, obtaining an automatic reflex for their stable rehabilitation. This apparatus is particularly adapted for bloodless and non-invasive correction of foot alterations allowing a quick, stable, final, rehabilitating and irreversible therapy of the non-malforming ailments of the arch of the foot, more particularly for the complete recovery of the flat or varus or valgus or sunken foot.

7 Claims, 10 Drawing Sheets

| RECORD OF CLINICAL TRIALS | | | | | |
|---|---|---|---|---|---|
| Pathology | | Total cases | Full recovery | Partial recovery | Unresolved cases |
| Flat foot | 1.st degree | 26 | 24 (92%) | – | 2 (8%) |
| | 2.nd degree | 108 | 68 (63%) | 40 (37%) | – |
| | 3.rd degree | 72 | 24 (33%) | 48 (67%) | – |
| Partial total | | 206 | 116 (63%) | 88 (35%) | 2 (2%) |
| Sunken foot | 1.st degree | 28 | 14 (50%) | – | 14 (50%) |
| | 2.nd degree | 34 | 10 (29%) | 24 (71%) | – |
| | 3.rd degree | 4 | – | 4 (100%) | – |
| Partial total | | 66 | 24 (26%) | 28 (57%) | 14 (17%) |
| Valgus foot | 1.st degree | 106 | 100 (94%) | – | 6 (6%) |
| | 2.nd degree | 72 | 66 (92%) | 6 (8%) | – |
| | 3.rd degree | 4 | 2 (50%) | 2 (50%) | – |
| Partial total | | 182 | 168 (79%) | 8 (19%) | 6 (2%) |
| Grand total | | 454 | 308 (56%) | 124 (37%) | 22 (7%) |

APPARATUS FOR THE BLOODLESS, NON-INVASIVE CORRECTION OF ALTERATIONS OF THE ARCH OF THE FOOT

The present invention relates to an apparatus for the correction of the non-malforming alterations of the foot such as flat, sunken, valgus and varus foot of various degrees, by means of electrostimulations.

The most common foot alteration occurs when the arch supporting the foot subsides. This defect is called by the specialists flat foot and is ranked at the second place only behind scoliosis in the score of orthopaedic troubles most worrying in the children growth, since it effects about 20% of the whole population. It involves not only aesthetic problems but causes also the loss of the foot regular function and this is a more serious problem. The methods for its solution are often inefficient. Half of the flat foots found during infancy heals up spontaneously because they are indeed slack foots. In this case the too elastic tissues subside under the infant's weight and simulate the flat foot. During growth however the foot becomes stronger and the trouble decreases until it disappears.

True flat foot is very different: the plantar vault, generally curved so as not to touch the ground on stepping, is flattened so that the entire sole leans on the ground. It is a defect involving bones, muscles and tendons, that does not improve in time. On the contrary this problem that is only aesthetic at the beginning, in the course of years causes even serious troubles of orthopaedic kind. Tendinitis, foot and ankle pain are the first consequences of flat foot. Moreover in time, incorrect stepping and running in view of flat foot, cause negative effects on knee, pelvis and even spine. Thus an ascending syndrome is generated, namely a trouble that starting from the extremities goes up to skeleton with a cascade effect with general articular and muscular consequences. Hence the importance of detecting true flat foots, namely those that improve only if they are treated.

Currently the methods used for the correction of the alterations of the plantar vault are mainly of two kinds: treatment with mobile orthoses or corrective shoes and surgical treatment.

The first method actually is only a prosthesis, namely it supports the relaxed arch of the foot without attaining any real improvement. Indeed most children undergoing this therapy, after some months having noticed no improvement, grow tired thereof and in agreement with the parents discontinue the treatment. The mobile prostheses generally consist of arch supports, and as such they should be worn for the lifetime. The same consideration apply to the black heavy orthopaedic shoe, hated by generations of children, which fortunately seems now to be obsolete. Also the mobile arch support and the recent American shell do not show any rehabilitative action. Such a first method is still today proven not to cause any corrective effect, but only a prosthetic effect so that it works until it is used, but when it is discontinued, the foot returns to its previous condition and therefore it is only a provisional support of the relaxed plantar vault.

In addition to that, one has to take into account the non-negligible cost, that often is borne by the National Health Service but many times by the family too.

The second method is certainly decisive in comparison with the first one. It is however a surgical operation and as such it has the risks connected with anaesthesia and complications arising during or after surgery, and therefore it may cause after effects such as ankylosis.

A great number of techniques were devised, but as it results also in the literature, there is no standard operation, thus tested and 100% or slightly less fail-safe because there is still uncertainty of the pathogenetic frame of the various kinds of flat foot.

In summary flat foot and all the other alterations of the foot rest are manifestations existing in a great number of children and adults.

The bloodless and non-invasive corrections, still used today, seem not to attain an actual correction of the foot alterations since they are simple prostheses only with a support function. Therefore, they neither cause the foot to do any active movement nor do they carry out a rehabilitative action.

On the other hand the surgical techniques resulted to be usable only in the few cases of serious deformity, being largely not advisable for the most common alterations such as the flexible pes planus.

A third conservative method is that of physiotherapy whose purpose is to give the patient, through a suitable program of exercises, the sensorial information needed to feel and maintain the correct position of the foot and to strengthen possible weakened muscles. This kind of physiotherapy, called proprioceptive, is advisable only for children of cooperative age, about from eight years onwards, but it is not exhaustive giving poor results. Moreover it is almost useless for adults.

As to the correction of other types of vault alteration such as varus valgus and sunken foot, there is no updated discussion in the literature with reference to resolutive non surgical therapies. For a general information of the known state of the art one should refer to the following publications: "Historical Review of flat foot surgery" by Prof. Bagliani of Alessandria, Italy and "Treatment of flat foot with orthesis and footwear" by Prof. Riccio of Naples, Italy.

The poor results obtained by the above mentioned methods pressed to test out innovative approaches in order to treat alterations of the arch of the foot. The resulting target of the intense research activity of the Applicant is the subject matter of the present invention. More particularly the considerable results obtained with the new method based on the use of electrostimulations supplied by the apparatus of the invention are described hereinafter. This innovative technique is absolutely bloodless and non-invasive, and on the basis of long and documented tests showed to give quick and irreversible results in the vast majority of treated cases.

Moreover this technique showed to overcome the limits of the mentioned conventional therapeutic methods, by giving quick and irreversible results in more than 90% of the cases affected by alterations that cannot be treated with the above mentioned methods.

Therefore Applicant started testing the apparatus of the present invention on the most common case, the flat foot, obtaining more than 90% of success for non structured cases, and in the structured cases normally intended for surgery, success was attained in at least 60% of the treated cases. Thereafter this method was extended to other types of alterations such as the pronated vagus foot, the sunken foot in all their degrees. This method resulted to be useful and operative also for adults and for all those conditions which in the meantime became a true pathology with a specific symptomatology, as for instance pain, easy trend to become tired and also lumbago and discopathy as a consequence of such alterations. It was now highlighted that these symptoms tend to disappear with great facility.

Object of the present invention is now an apparatus for the correction of the non-malforming alterations of the foot (flat, sunken, valgus and varus foot of various degrees) by means of electrostimulations. The method applied through the above-mentioned apparatus is based on its emissions of electrostimulations with stepwave shape at pulsed rate of variable duration and amplitude.

More particularly the present invention relates to an apparatus for the bloodless and non-invasive correction of the non-malforming alterations of the foot characterized by comprising:

a) a source of electrical currents with multiple step wave shapes at pulsed rate of variable duration and amplitude;

b) that source being connected to electrodes to be placed on the body of the patient to be treated;

c) detector means of the electric resistance existing at the ends of those electrodes during use of the apparatus;

d) means for measuring and transducing data supplied by the detectors; and e) means for processing the data supplied by said detectors c) through said means (d) for the self regulation of the generated wafe shapes.

The apparatus generates a particular type of wave called S wave, allowing to act in a very specific way on clearly defined muscular groups. This wave consists of three periodically repetitive phases. During the first phase of the duration of tens of milliseconds, tipically 50 ms, the apparatus supplies a current with peak values in the order of milliampere (mA) fractions. This signal allows the depolarization of the muscle membrane or the muscular lumdles to be treated and prepares them to the reception of the signal applied in the subsequent phase.

The actual muscle stimulation occurs in the second phase through a signal of greater duration, tipically a double duration in comparison with the preceding one and with an amplitude of some mA, up to tens mA according to the patient. The apparatus allows the variation of duration and amplitude, of the electric signals applied in said phases. The choice of these parameters depend from: 1) patient age 2) type of alteration to be treated and 3) cycle of therapy being carried out. In the third phase, the signal is zeroed so as to allow the relaxation of muscular lumdles. This phase has the greatest duration in the order of 1 second. The total wave frequency is in the order of one cycle/second (1 Hz).

The apparatus developed by Applicant is provided with a system for measuring in situ the emitted signals and uses also an integrated software giving the values of the specific parameters for each patient under therapy.

The S wave is adapted to generate, through a proprioceptive and an exteroceptive route, a so-called myotatic reflex, that is to say a deep osteotendinous and tendinomuscular reflex, derived from the stimulation of the muscular and tendinous receptors, that through the production of an active contraction, acts on the muscles responsible of the alteration. The repetition of such a contraction produces a repetitive motor gesture. In time this produces in turn a reflex movement creating in the patient a new guide image of his corporeal scheme. This final modification causes in the patient a new and more precise idea of his body segments.

The confirmation of the foregoing affirmation derives from the methodical and deep tests carried out. After one year from the tests it was found that the patient not only keeps the acquired tone and morphology but even shows further improvements.

The objective picture formed at the end of the treatment with the apparatus according to the present invention carded out as an average for about 20 days, highlighted the following:

a) a correction of the deambulation;

b) disappearance of the tiredness feeling and pain;

c) better distribution of the load, evaluated by using a computerized baroscope.

For the above mentioned reasons the method that can be obtained with the apparatus of the present invention, can be applied to patients of an age from 5 years onward, and it is successful also in the adults.

A detailed and non limiting description of a particular embodiment of the subject matter of the present invention is given hereinafter, with reference to the various figures of the attached drawings, however without impairing the general principles of the invention.

FIGS. 11a and 11b show the same details but for a SX sunken foot of $3^{rd}$ degree, DX sunken foot of $2^{nd}$ degree.

The basic idea of the invention arises from the recognition that the flat foot, namely the most common alteration to be found for the foot, can be substantially ascribed to an innatural relaxation of the arch of the foot, whose tendinous structure is poorly supported by invigorated muscular bundles; obviously this occurs in contrast with what is required by any musculotendinous tract of the human body.

It was also shown that most flat-footed patients have also a relaxed posture of the whole body; such a posture therefore can be correlated to a wrong corporal image that the patient receives from his whole body, thus also from his foot.

The treatment obtained by the apparatus consists in being able to evoke the so-called myotatic reflex by means of a set of rapid and time limited stretchings induced by suitable electrostimulation.

The object is to generate by subsequent applications a reflex arch that in time may turn into an automatic movement, so as to cause a stabilization and invigoration of the relaxed muscles.

The stimulation technique obtained from the apparatus of the invention is deemed to comprise also a contemporaneous modification of the corporeal image received of the treated zone.

The method of the present invention is characterized by the use of particular electrostimulations with double stepped wave shapes at a pulsed rate. A first current pulse allows the depolarization of the muscular membrane. This causes the muscle to be more reactive to the second pulse. The therapeutic action is based on the stimulation effected by said second pulse. The current pulses used have a peak value of few tens milliamperes, duration of hundreds milliseconds and repetition frequences of about 1 Hz.

The apparatus according to the invention allows also the variation of the wave form and of its characterizing parameters as well as the selfregulation of the optimal current values applied through feedback mechanisms carried out by measuring in situ the resistance present at the electrodes.

Figure 1A:
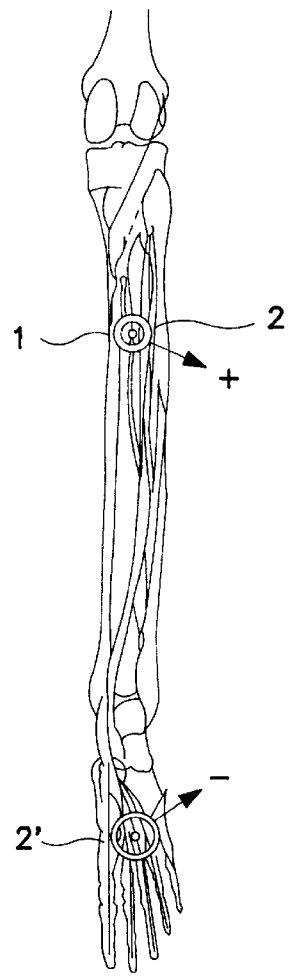
FIGS. 1a, 1b, 1c show the arrangement on the patient of the positive and negative electrodes in the various pathologies, in case of flat foot, varus and valgus foot and sunken foot, respectively.
Figure 1B:
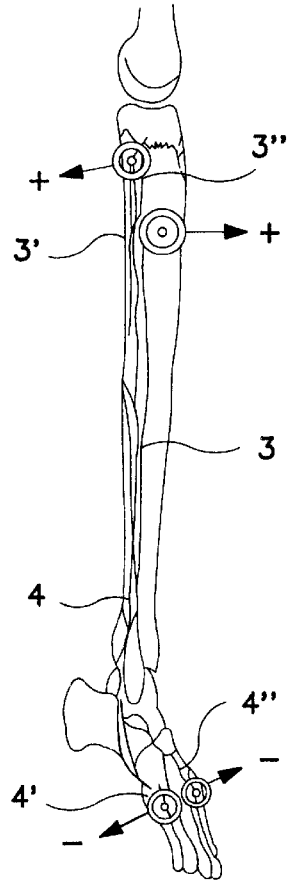
Figure 1C:
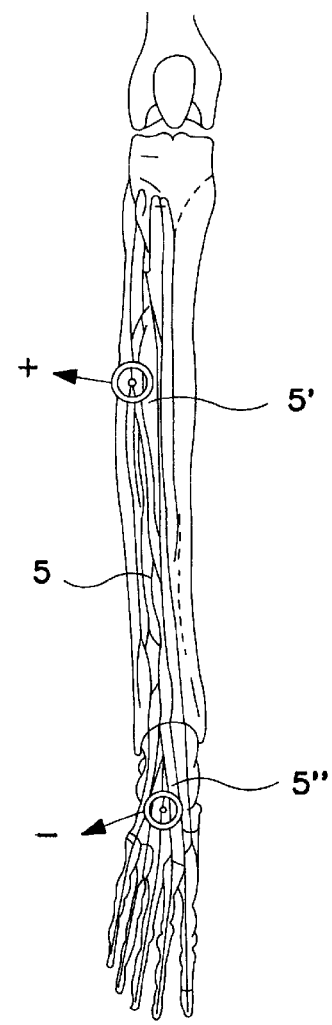

The electrodes are arranged at various points of the patient's leg and foot according to the kind of alteration as shown in FIGS. 1a, 1b, 1c.

In case of flat foot the positive electrode + is arranged at the upper part of the toe flexor longus muscle 1 and rear tibial muscle 2 and the negative electrode − at the base of the toes 2', FIG. 1a:

In case of varus foot, the positive electrode + is arranged on the upper part of the leg 3' near the peroneal long muscle 3 while the negative electrode − is arranged at the lower end 4' of the peroneal brevis muscle 4, FIG. 1b;

In case of valgus foot however the positive electrode + is arranged at the upper end 3" of the peroneal longus muscle 3 and the negative electrode − at the base of the toes 4" near the peroneal brevis muscle 4, FIG. 1b; at last in case of sunken foot the positive electrode + is arranged at the upper part 5' of the toe extensor longus muscle 5 while the negative electrode − is arranged on the foot instep, FIG. 1c.

In a more significant embodiment, the apparatus of the present invention, described hereinafter only as an example without limiting in any way the general scope of the invention, comprises a signal generator 6, generally at 12 Volts, connected to the mains 8, generally at 220 Volts, through a transformer 7, FIG. 2; the current thus generated for the electrostimulation has a multiple step wave form at pulsed rate; more particularly, the wave comprises three constant or variable phases, the first having a duration in the order of tens of milliseconds and a peak value in the order of mA fractions, called depolarization phase, the second phase having a greater duration, tipically the double, for muscle stimulation with an amplitude between some units and tens mA, and the third, relaxation phase having a duration of one second and zero amplitude, respectively, see FIG. 3. The current goes through the control switch board 9 to the electrodes + and − that are arranged in predetermined areas of patient's leg and foot according to the therapy to be followed, see FIGS. 1a, 1b, 1c; said electrodes +, − are provided at their end with in situ detectors 10, 10' of the patient's electric resistance, generally consisting of lead plates, whose values taken by measuring devices 11, 11' are fed through transducers 12, 12' to programmable microcontrollers made of integrated solid state vacuum electronic circuits 13, namely microprocessors with system software for their processing together with the data of the patient's card supplied by an external computer 14 so as to provide for the self regulation of the optimal values of the applied parameters of current through interactive feedback processes.

Figure 2:
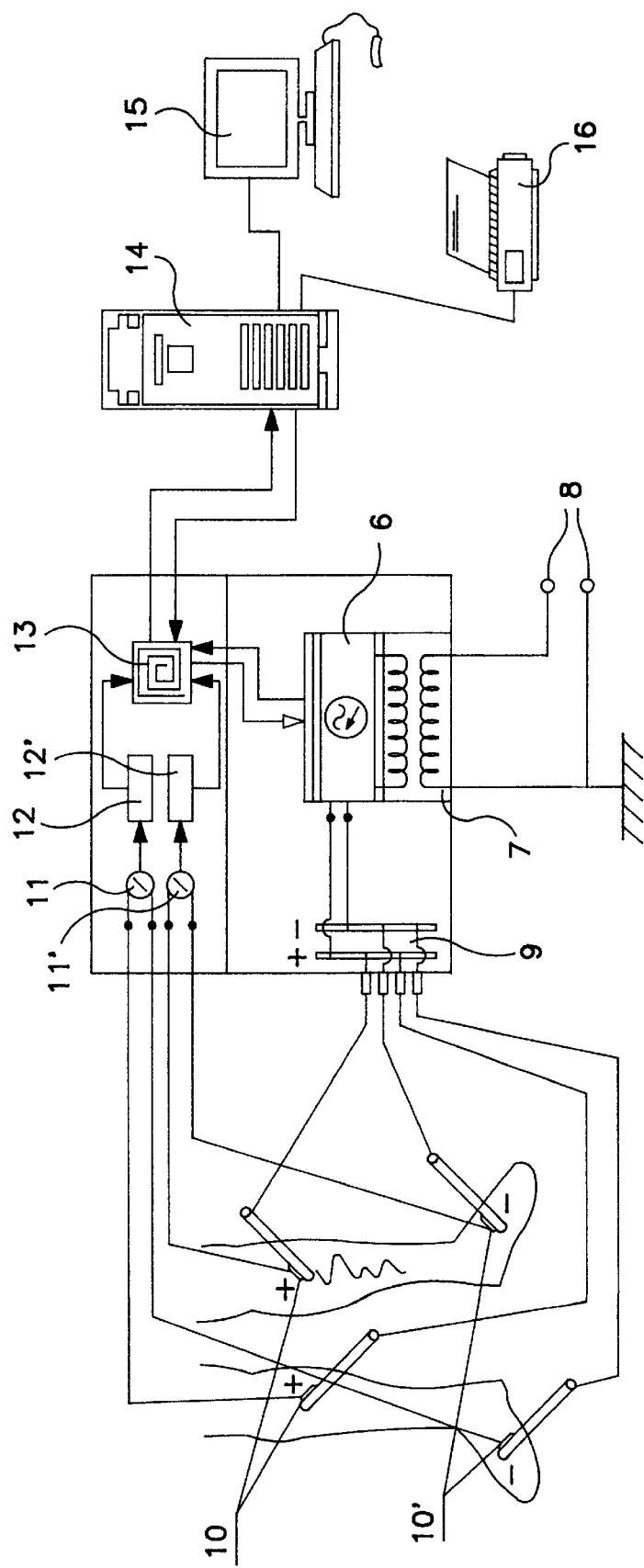
FIG. 2 shows a scheme of the elements and functions constituting the apparatus.

All the parameters useful for the process relating to the therapy of a predetermined patient, are then processed and stored by the external computer and can be displayed through monitor 15 or printed by the printer 16, FIG. 2.

Flat foot of babies is a physiological phenomenon and this remains at least until the infant begins to walk and therefore to form the supports. Only after such a period it is possible to diagnose the presence of a true flat foot. For this reason, any possible treatment starts only from the average age of 4 years. The description of a therapy protocol implemented by using the apparatus of the present invention is given hereinafter.

The method consists of a first stage in which a plantography is obtained, to be effected not earlier than an age of 3.5–4 years for the above mentioned reasons.

The plantographic examination shows the degree of foot alteration.

The second stage consists of the actual treatment, that requires generally at least 10 applications, with a second plantographic control to be conducted at the middle of the therapy.

Finally a third plantography is conducted in order to decide whether to terminate the therapy or to continue with additional applications.

The third and last stage provides for a follow-up with a first plantographic control after two months, followed by checks every semester in order to establish the possible necessity of little boosting applications. The follow-up stage must be carried out for at least two years.

The validity of the technique based on the apparatus of the present invention is largely proved by the positive results obtained in more than 90% of the patients affected by flat or sunken or valgus foot that underwent this therapy.

Significant examples of plantographies effected before and after the treatment of patients affected by alterations of the three types, are the most eloquent confirmation of this success as shown in FIGS. 6 to 11.

Figures 3, 4:
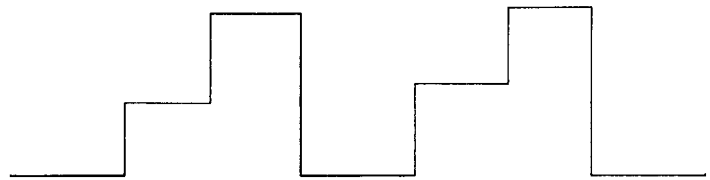
FIG. 3 shows the particular wave forms generated by the apparatus source.
FIG. 4 is a statistic table relating to two years of clinical trials, for pathologies of different degrees for three types of alterations.
Figure 5:
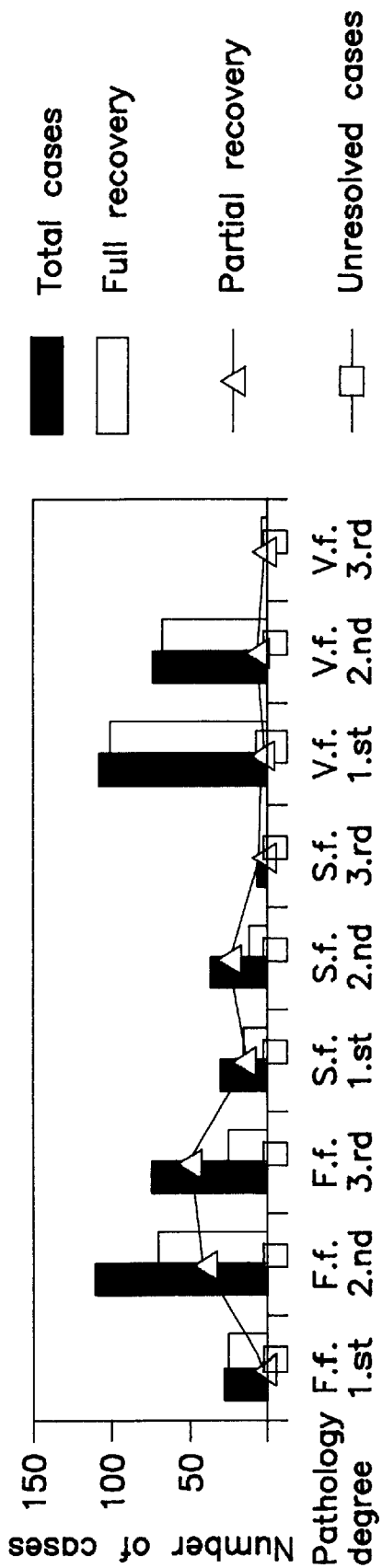
FIG. 5 shows the statistical data of the clinical trials in a graphic form.
Figure 6B:
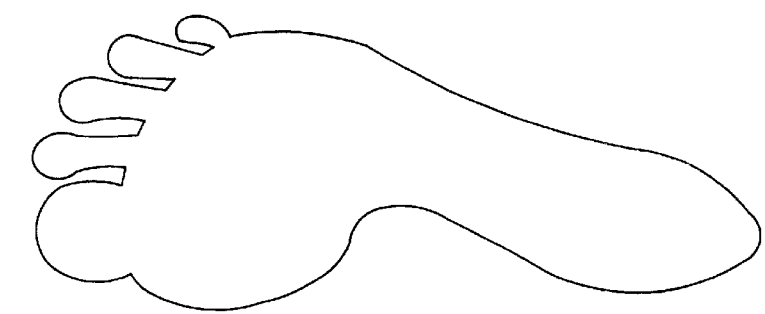
FIGS. 6a and 6b show drawings taken from the corresponding plantographies, of the soleprints before and after the treatment with electrostimulations of the apparatus for a bilateral flat foot of $2^{nd}$ degree, clearly showing the obtained recovery result.
Figure 6B:
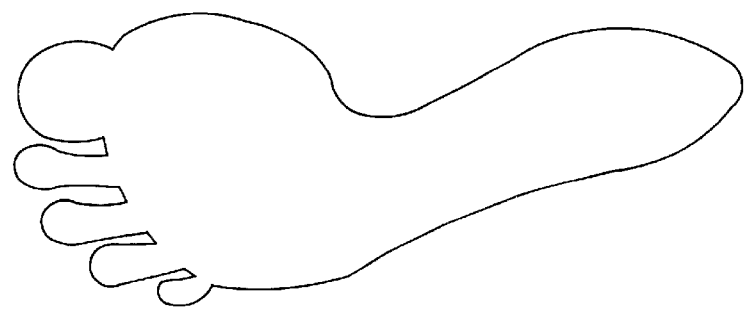
Figure 6A:
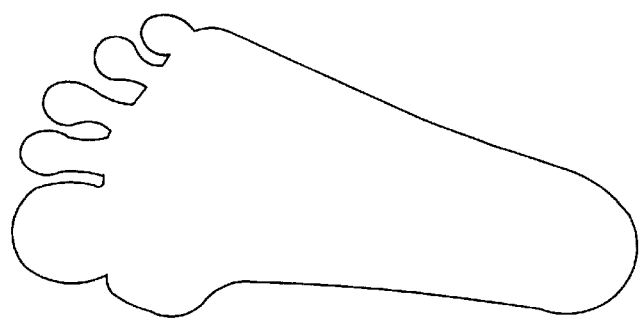
Figure 6A:
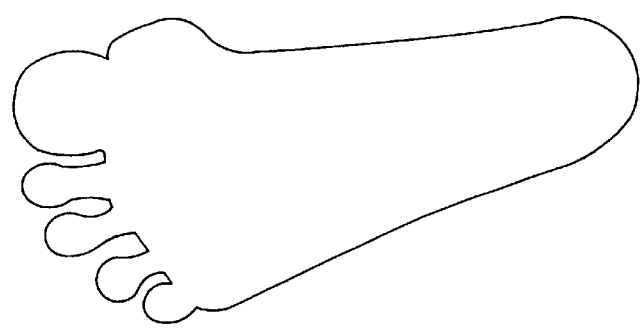
Figure 7B:
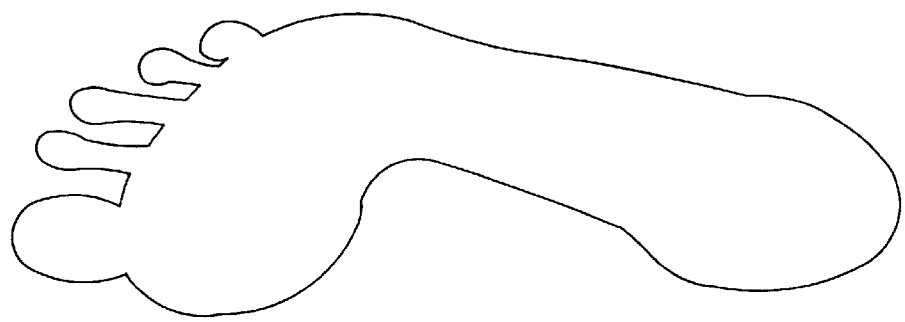
FIGS. 7a and 7b show the same details but for a SX flat foot of $2^{nd}$ degree, DX flat foot of $3^{rd}$ degree.
Figure 7B:
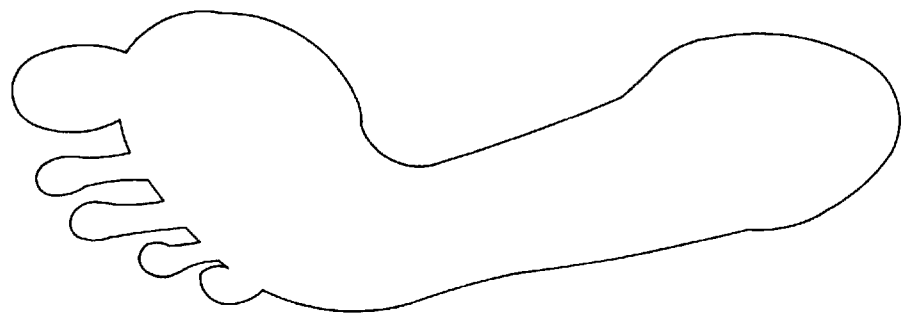
Figure 7A:
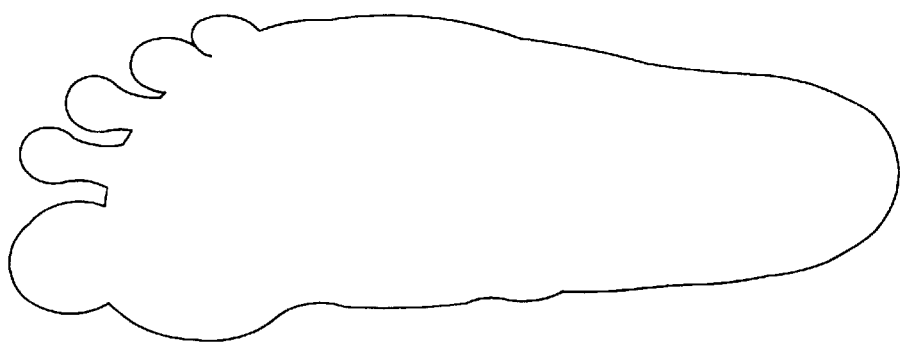
Figure 7A:
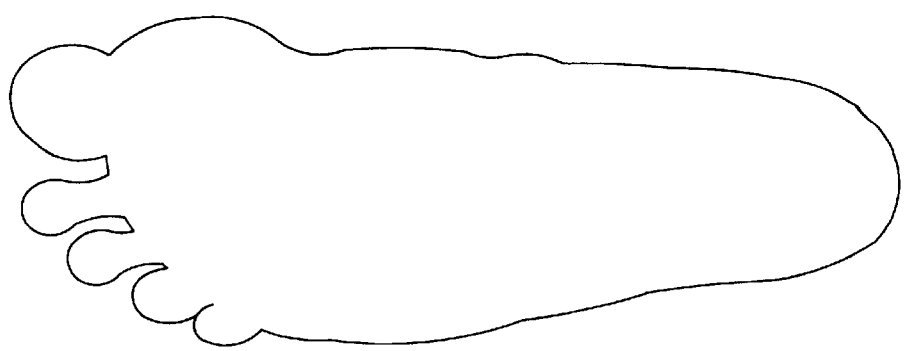
Figure 8B:
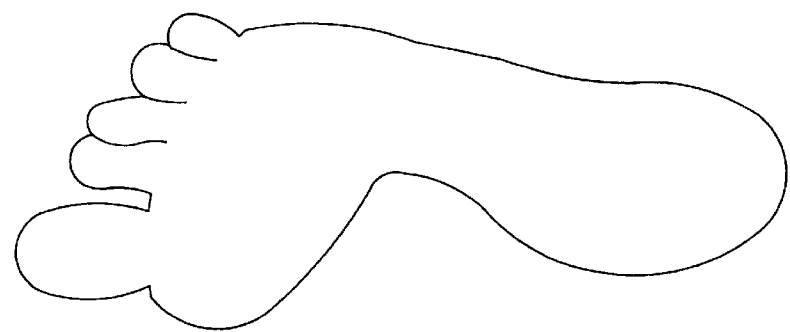
FIGS. 8a and 8b show the same details but for a bilateral flat-valgus foot of $2^{nd}$ degree.
Figure 8B:
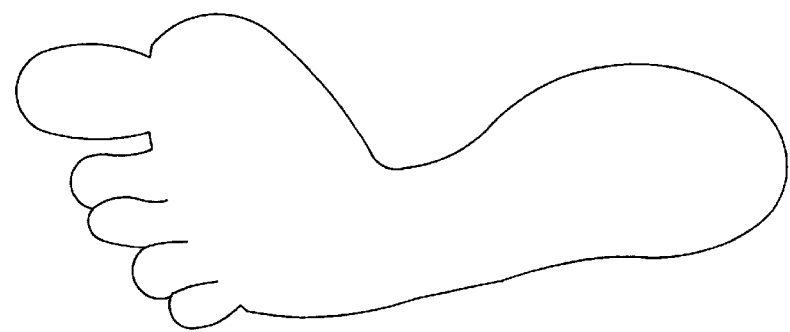
Figure 8A:
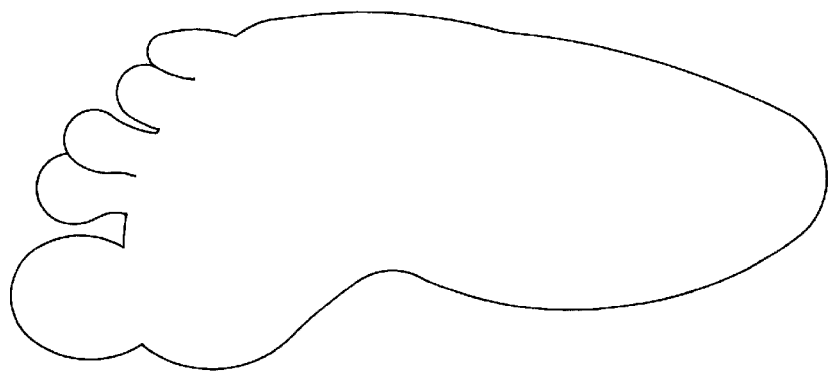
Figure 8A:
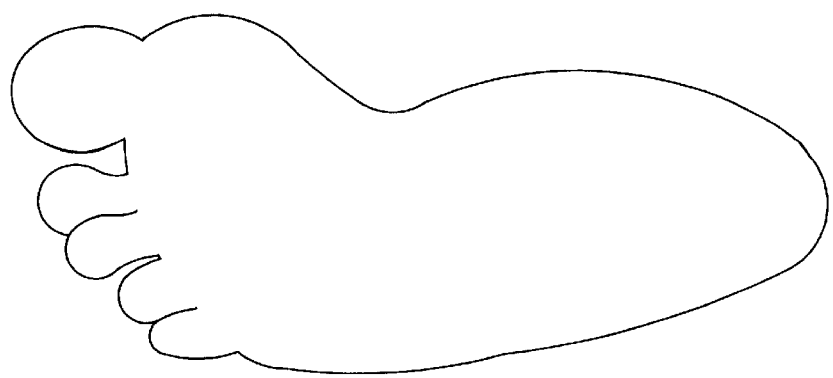
Figure 9B:
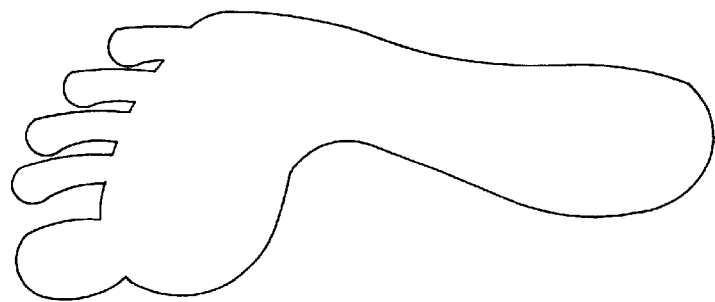
FIGS. 9a and 9b show the same details but for a SX flat foot of $2^{nd}$ degree, DX flat foot of $2^{nd}$ degree and valgus foot of $1^{st}$ degree.
Figure 9B:
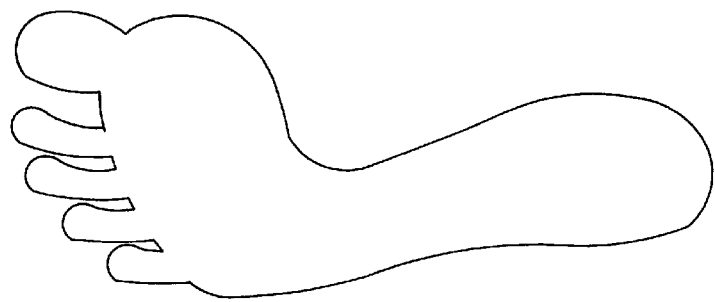
Figure 9A:
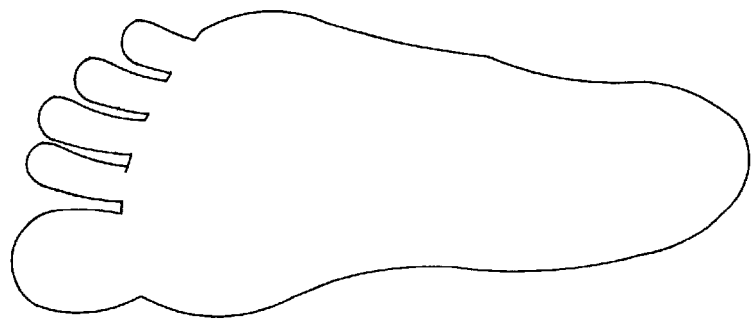
Figure 9A:
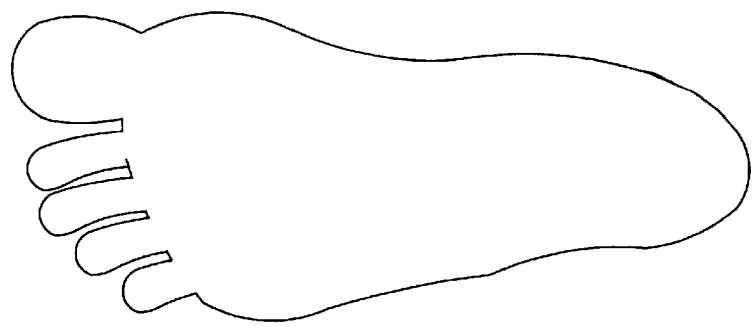
Figure 10B:
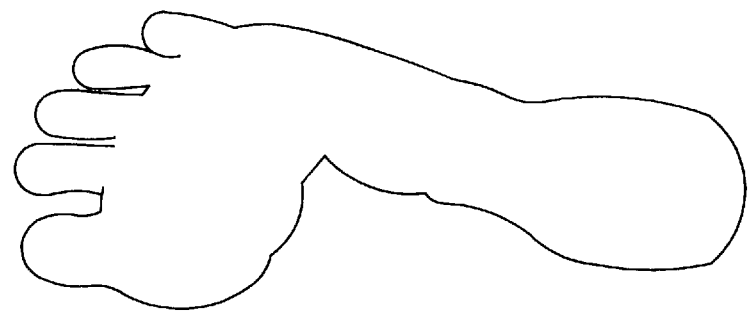
FIGS. 10a and 10b show the same details but for a SX flat foot of $3^{rd}$ degree, DX flat foot of $2^{nd}$ degree and valgus foot of $1^{st}$ degree.
Figure 10B:
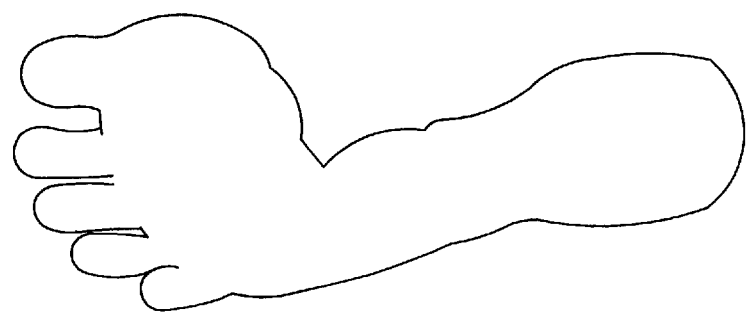
Figure 10A:
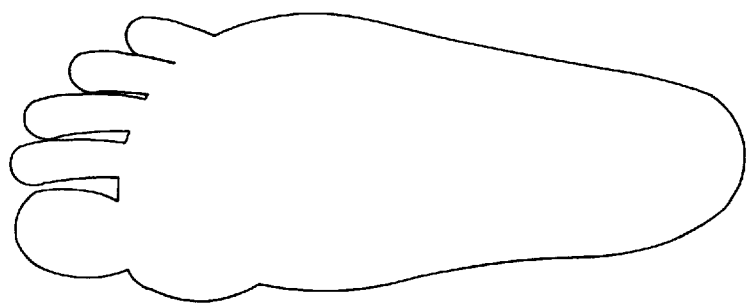
Figure 10A:
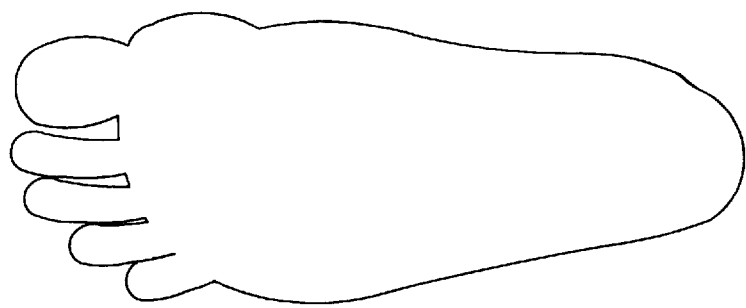
Figure 1L:
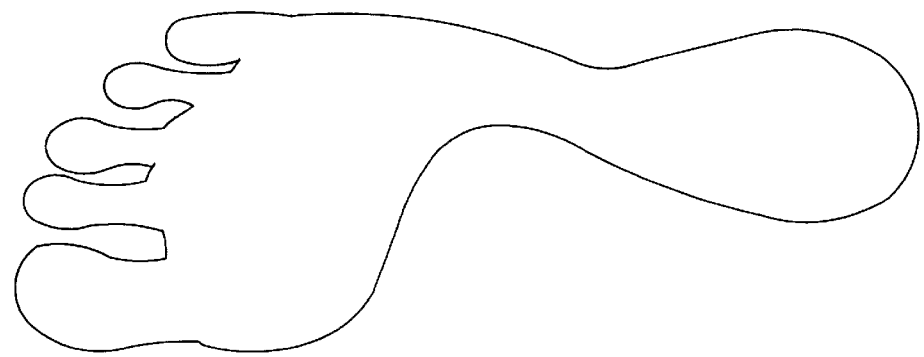
Figure 1L:
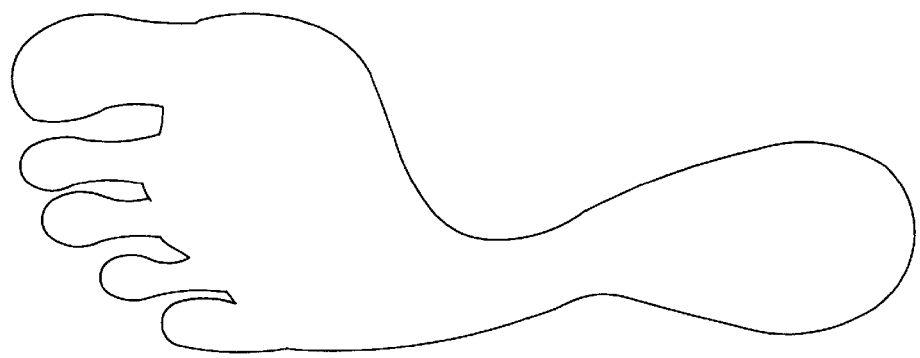
Figure 1L:
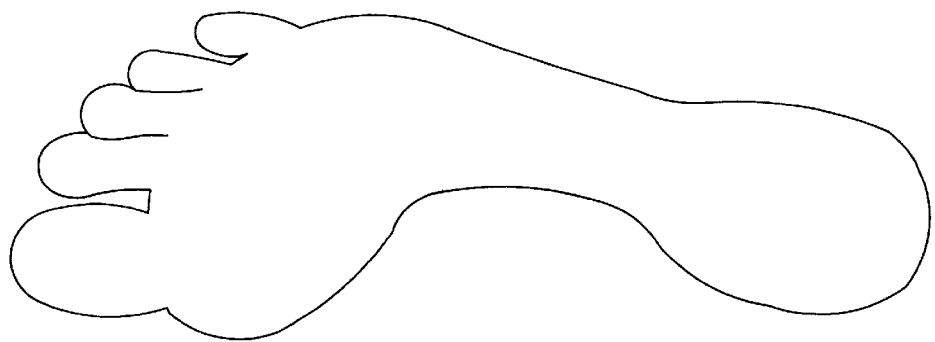
Figure 1L:
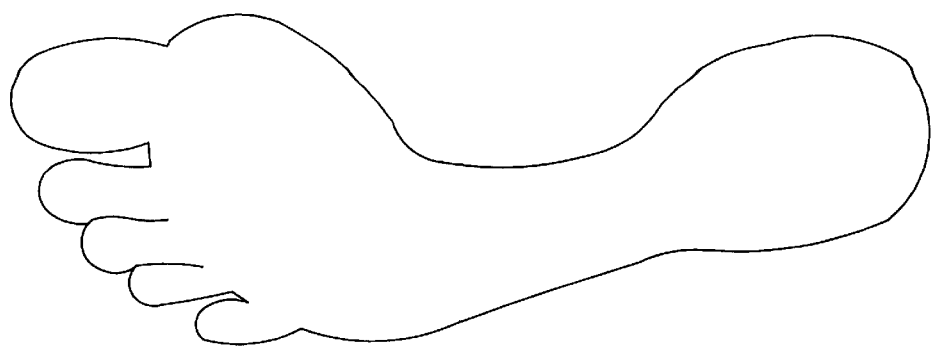

The statistics relating to the record of clinical trials shown in graphic form in FIG. 5 and table of FIG. 4, shows the high percentages of full recovery recorded in cases of flat foot (63%) and valgus foot (79%) of various degrees.

The remaining patients affected by the mentioned pathologies have in any case shown improvements in the degree of alteration, see the item "partial recovery" in the table of FIG. 4, excepting a 2% of them that did not benefit from the treatment.

Greater difficulties were found in the treatment of patients affected by sunken foot with a total of 17% of unresolved cases.

It is to be underlined that a great part of the alterations treated and successfully corrected had been judged irrecoverable with the traditional bloodless methods.

A further confirmation of the rehabilitation character of the therapy comes from the acknowledgment that for many treated cases, the plantographic controls effected one year after termination of the first treatment cycle, showed the presence of further improvements of the structure of the arch of the foot in comparison with the checkup conducted at the cycle end.

Very slight regressions, however corrected quickly with further cycle of therapy, where detected only in 10% of cases.

The reported statistical data relate above all to patients up to 10–11 years of age. Statistics relating to pathologies of the first degree concern only patients of a sufficiently advanced age so as not to expect physiological improvements connected with growth.

Finally, trials conducted on adult patients gave particularly significant results, which are not discussed in the present description for sake of conciseness.

What is claimed is:

1. Apparatus for the bloodless and non-invasive correction of the non-malforming alterations of the foot comprising:

a. a source of electrical currents with multiple step wave forms at pulsed rate with variable duration and amplitude;
b. said source being connected to electrodes (+, −) to be arranged on the body of the patient to be treated;
c. detector means of electrical resistance at the ends of said electrodes (+, −) during use of the apparatus;
d. measuring and transducing means for the data supplied by said detector means; and
e. means for processing the data supplied by said detector means through said means for self-regulation of the generated wave forms.

2. Apparatus for the correction of foot alterations according to claim 1, characterized by the fact that the source of electrical currents consists of a generator based on solid state vacuum integrated electronic circuits with programmable microcontrollers.

3. Apparatus for the bloodless and non-invasive correction of the foot alterations according to claim 1, comprising microprocessor means with integrated system software to allow the variation of the wave form and of its characterizing parameters as well as self-regulation of the optimal current values applied through interactive feedback processes, effected through inputs of said detecting means and said measuring means in situ of the resistance present at the electrodes (+, −) during use.

4. Apparatus for the correction of the alterations of the arch of the foot according to claim 1, characterized by the fact that the electrostimulation produced by the source of electric currents at pulsed rate, has a double step, the first pulse being directed to the depolarization of the muscular membrane, the second pulse being directed to the stimulation made more reactive by the preliminary action effected by the first pulse.

5. Apparatus for the correction of the alterations of the arch of the foot according to claim 1, characterized by the fact that the electric wave produced by the current source (6) comprises three constant or variable, periodically repetitive phases, the first depolarization phase having a duration of tens of milliseconds, and a peak current value in the order of milliamperes, the second stimulation phase having a greater duration and amplitude in the order of milliamperes, and a third relaxation phase having a much greater duration and zero amplitude.

6. Apparatus for the correction of the alterations of the arch of the foot according to claim 5, characterized by the fact that the depolarization signal has a duration of 50 ms and a current peak value in the order of milliampere fractions, the stimulation signal has a double duration and an amplitude between some mA and tens mA, and the relaxation phase a duration of about one second and zero amplitude, respectively, the total repetition frequence being in the order of one cycle per second.

7. Apparatus for the correction of the alterations of the arch of the foot according to claim 1, characterized by the fact that the electric wave is generated by a current or voltage source.

* * * * *